United States Patent
Yamano et al.

(10) Patent No.: US 11,977,681 B2
(45) Date of Patent: May 7, 2024

(54) INFORMATION PROCESSING DEVICE AND INFORMATION PROCESSING METHOD

(71) Applicant: SONY GROUP CORPORATION, Tokyo (JP)

(72) Inventors: Ikuo Yamano, Tokyo (JP); Daisuke Tajima, Tokyo (JP); Yohei Fukuma, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 17/905,656

(22) PCT Filed: Mar. 2, 2021

(86) PCT No.: PCT/JP2021/007885
§ 371 (c)(1),
(2) Date: Sep. 6, 2022

(87) PCT Pub. No.: WO2021/182176
PCT Pub. Date: Sep. 6, 2021

(65) Prior Publication Data
US 2023/0350491 A1    Nov. 2, 2023

(30) Foreign Application Priority Data
Mar. 13, 2020    (JP) .................................. 2020-044466

(51) Int. Cl.
*G06F 3/01*    (2006.01)
*G06F 3/0346*    (2013.01)

(52) U.S. Cl.
CPC ............ *G06F 3/014* (2013.01); *G06F 3/0346* (2013.01)

(58) Field of Classification Search
CPC .............................. G06F 3/014; G06F 3/0346
See application file for complete search history.

(56) References Cited

U.S. PATENT DOCUMENTS

| | | | | |
|---|---|---|---|---|
| 2016/0054797 | A1* | 2/2016 | Tokubo | G06F 3/0346 345/633 |
| 2016/0134299 | A1* | 5/2016 | Lowe | G06F 3/016 341/15 |

(Continued)

FOREIGN PATENT DOCUMENTS

| | | |
|---|---|---|
| JP | 2012-073830 A | 4/2012 |
| JP | 2015-121979 A | 7/2015 |

(Continued)

OTHER PUBLICATIONS

International Search Report and Written Opinion of PCT Application No. PCT/JP2021/007885, dated May 11, 2021, 09 pages of ISRWO.

*Primary Examiner* — Muhammad N Edun
(74) *Attorney, Agent, or Firm* — CHIP LAW GROUP

(57) ABSTRACT

An information processing device includes: a first detection unit that detects contact of fingertips on the basis of an output waveform of an acceleration sensor; a second detection unit that detects the contact of the fingertips on the basis of a change in electrostatic capacitance; and an operation control unit that causes the first detection unit to operate in a case of detecting timing at which the fingertips come into contact with each other, and causes the second detection unit to operate in a case of detecting timing at which the fingertips are separated from each other.

18 Claims, 11 Drawing Sheets

OFF STATE    ON STATE

(56) References Cited

U.S. PATENT DOCUMENTS

| | | | |
|---|---|---|---|
| 2016/0363997 A1* | 12/2016 | Black | G06F 3/014 |
| 2019/0101981 A1* | 4/2019 | Elias | A41D 19/00 |
| 2020/0257362 A1* | 8/2020 | Wang | G06F 3/011 |

FOREIGN PATENT DOCUMENTS

| | | | |
|---|---|---|---|
| JP | 2016-170581 A | 9/2016 |
| JP | 2019-075034 A | 5/2019 |
| JP | 2019-526864 A | 9/2019 |
| WO | 2018/110432 A1 | 6/2018 |
| WO | 2019/077652 A1 | 4/2019 |

* cited by examiner

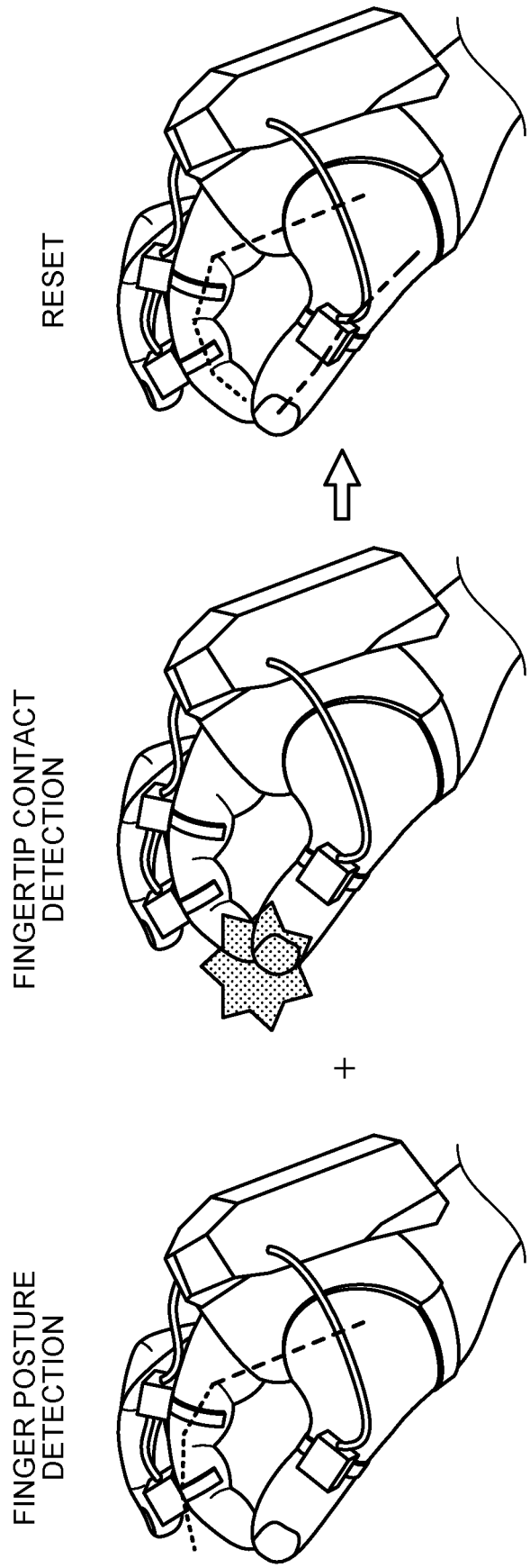

INFORMATION PROCESSING DEVICE AND INFORMATION PROCESSING METHOD

CROSS REFERENCE TO RELATED APPLICATIONS

This application is a U.S. National Phase of International Patent Application No. PCT/JP2021/007885 filed on Mar. 2, 2021, which claims priority benefit of Japanese Patent Application No. JP 2020-044466 filed in the Japan Patent Office on Mar. 13, 2020. Each of the above-referenced applications is hereby incorporated herein by reference in its entirety.

FIELD

The present invention relates to an information processing device, an information processing method, and an information processing program.

BACKGROUND

Examples of movements of fingers which movements are used for hand interaction include contact between fingertips, such as contact between an index finger and a thumb. As examples of a method of detecting such fingertip contact, electrostatic touch detection for detecting the fingertip contact from a change in electrostatic capacitance, acceleration waveform detection for detecting the fingertip contact from a waveform of an acceleration sensor, and the like are known.

CITATION LIST

Patent Literature

Patent Literature 1: WO 2018/110432 A

SUMMARY

Technical Problem

However, since both of the electrostatic touch detection and the acceleration waveform detection have advantages and disadvantages, there is one aspect that it is difficult to robustly detect the fingertip contact.

Thus, the present disclosure is to provide an information processing device, an information processing method, and an information processing program capable of realizing robust detection of fingertip contact.

Solution to Problem

According to the present disclosure, an information processing device includes a first detection unit that detects contact of fingertips on a basis of an output waveform of an acceleration sensor, a second detection unit that detects the contact of the fingertips on a basis of a change in electrostatic capacitance, and an operation control unit that causes the first detection unit to operate in a case of detecting timing at which the fingertips come into contact with each other, and causes the second detection unit to operate in a case of detecting timing at which the fingertips are separated from each other.

BRIEF DESCRIPTION OF DRAWINGS

FIG. 8 is a view illustrating an example of a method of resetting the posture of the finger.

DESCRIPTION OF EMBODIMENTS

Figure 1:
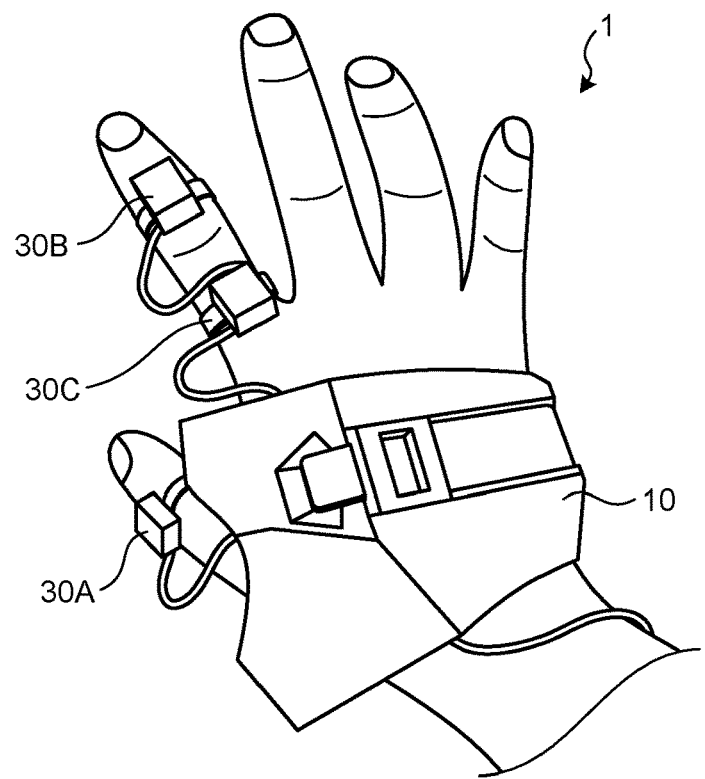
FIG. 1 is a view illustrating an example of an external appearance of a controller according to one embodiment.

In the following, embodiments of the present disclosure will be described in detail on the basis of the drawings. Note that in each of the following embodiments, overlapped description is omitted by assignment of the same reference sign to the same parts.

Also, the present disclosure will be described in the following order of items.

1. External appearance of a controller
2. Hand interaction
2-1. Sensors used for fingertip contact detection
2-2. Sensors used for finger posture detection
3. One aspect of a problem
4. One aspect of an approach to problem solving
5. Functional configuration of a controller main body 10
5-1. Posture detection unit
5-2. Operation control unit
5-2-1. First detection unit
5-2-2. Second detection unit
5-3. Reset unit
5-4. Output unit
6. Processing procedure of a controller 1
7. One aspect of an effect
8. Application example
9. Modification example
10. Hardware configuration

1. External appearance of a controller

Figure 2:
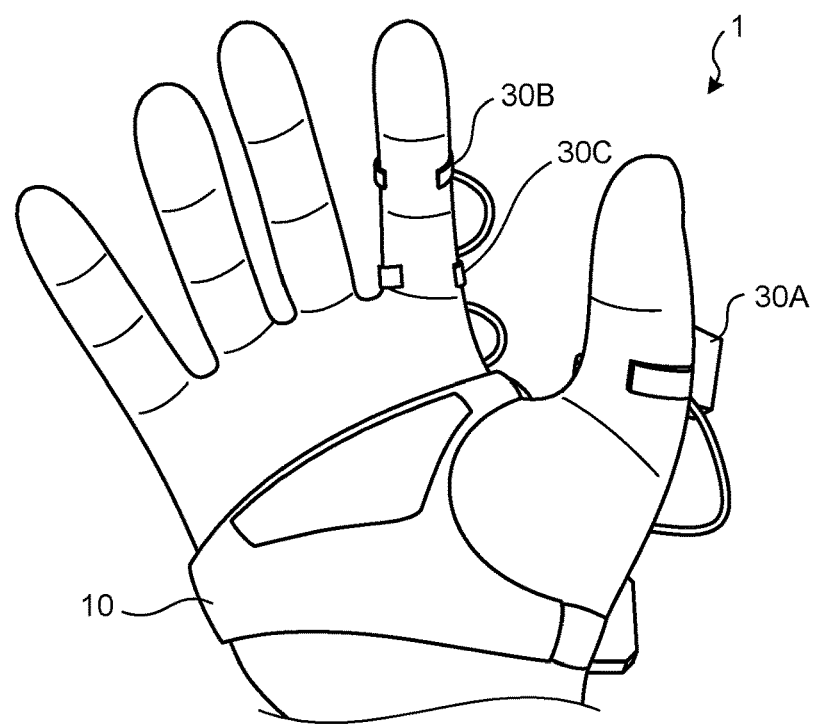
FIG. 2 is a view illustrating the example of the external appearance of the controller according to the one embodiment.

FIG. 1 and FIG. 2 are views illustrating an example of an external appearance of a controller according to one embodiment. An external appearance of a controller 1 mounted on a right hand as viewed from a back side of the hand is illustrated in FIG. 1, and an external appearance of the controller 1 as viewed from a side of a palm is illustrated in FIG. 2.

The controller 1 illustrated in FIG. 1 and FIG. 2 is to realize hand interaction for operating content reproduced by a technology such as augmented reality (AR) or virtual reality (VR), for example. Although an example of operating AR content or VR content has been described herein, this is merely an example. In addition, the hand interaction can be applied to overall operation of a three-dimensional model, such as a three-dimensional object on a display, a robot operation, or a three-dimensional mouse.

As illustrated in FIG. 1 and FIG. 2, the controller 1 may include a controller main body 10, a thumb part 30A, an index finger part 30B, and an index finger part 30C.

Hereinafter, the thumb part 30A, the index finger part 30B, and the index finger part 30C may be referred to as "finger parts 30" in a case where individual identification thereof is not necessary.

These controller main body 10 and finger parts 30 may be configured in any connection form regardless of a wired or wireless manner, and may be configured in such a manner that transmission can be performed via an input/output interface, a communication interface, or a network, for example.

Here, the controller 1 is superior to an existing data glove and the like in a point that a structure of making fingertips and a palm side free is included. As a result, not only operation of a virtual object but also compatibility between operation of a real object and the operation of the virtual object are made possible.

For example, as illustrated in FIG. 2, a band that fixes the controller main body 10 is formed in such a manner as to cover a hypothenar eminence and a hamate bone. As a result, since the controller main body 10 can be mounted in a state in which a thenar eminence is exposed, it is possible to prevent a movement of a thumb from being hindered by the controller main body 10.

In addition, a structure that makes a fingertip free and that does not hinder a movement of a joint is employed for the finger parts 30. As illustrated in FIG. 1, each of the finger parts 30 is formed in a manner of being mountable from an upper portion of a proximal phalanx or middle phalanx of a finger. For example, the thumb part 30A is mounted on a proximal phalanx of a thumb. Also, the index finger part 30B is mounted on a middle phalanx of an index finger. Furthermore, the index finger part 30C is mounted on the proximal phalanx of the index finger.

Figure 3:
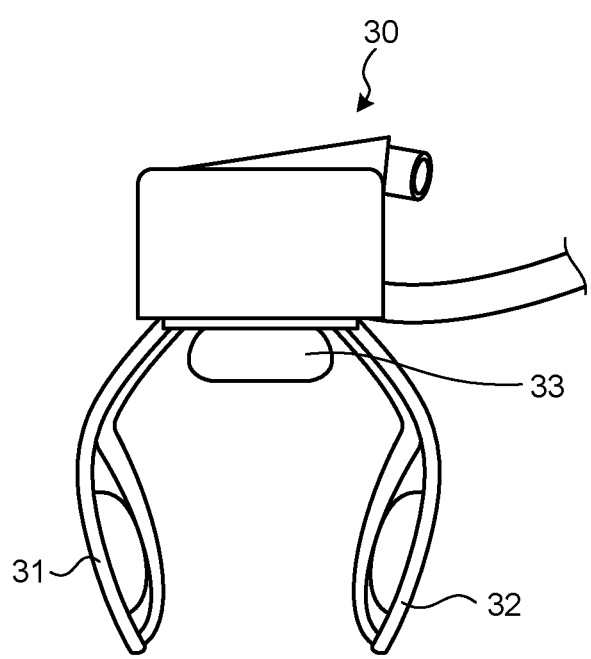
FIG. 3 is a front view of a finger part.

FIG. 3 is a front view of a finger part. As illustrated in FIG. 3, each of the finger parts 30 includes a C-shaped locking member. For example, the C-shaped locking member supports an upper surface portion and side surface portion of a proximal phalanx or a middle phalanx of a finger at three points that are elastic members 31 and 32 at both right and left ends and an elastic member 33 at the center. With such three-point support, the finger part 30 can be mounted in a state in which a finger pulp is exposed.

<<2. Hand Interaction>>

Figure 4:
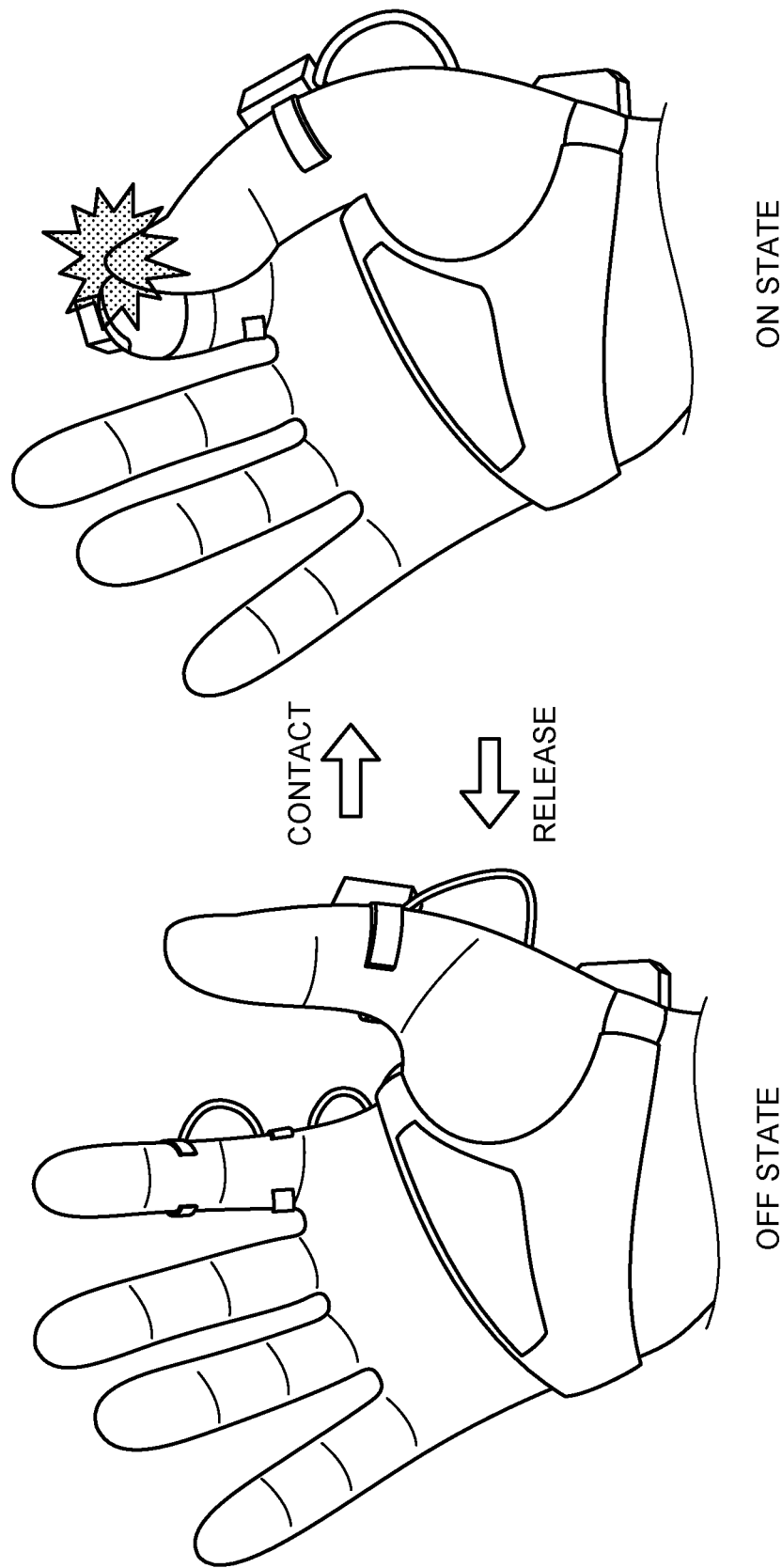
FIG. 4 is a view illustrating an example of an ON state and an OFF state of fingertip contact.

From an aspect of realizing the hand interaction, the controller 1 performs "fingertip contact detection" of detecting contact between fingertips, such as contact between an index finger and a thumb. FIG. 4 is a view illustrating an example of an ON state and an OFF state of fingertip contact. The OFF state and the ON state of the fingertip contact are illustrated side by side in FIG. 4. As illustrated in FIG. 4, the fingertip contact transitions from the OFF state to the ON state at timing at which the thumb and the index finger come into contact, and the fingertip contact transition from the ON state to the OFF state at timing at which the thumb and the index finger are separated.

Figure 5:
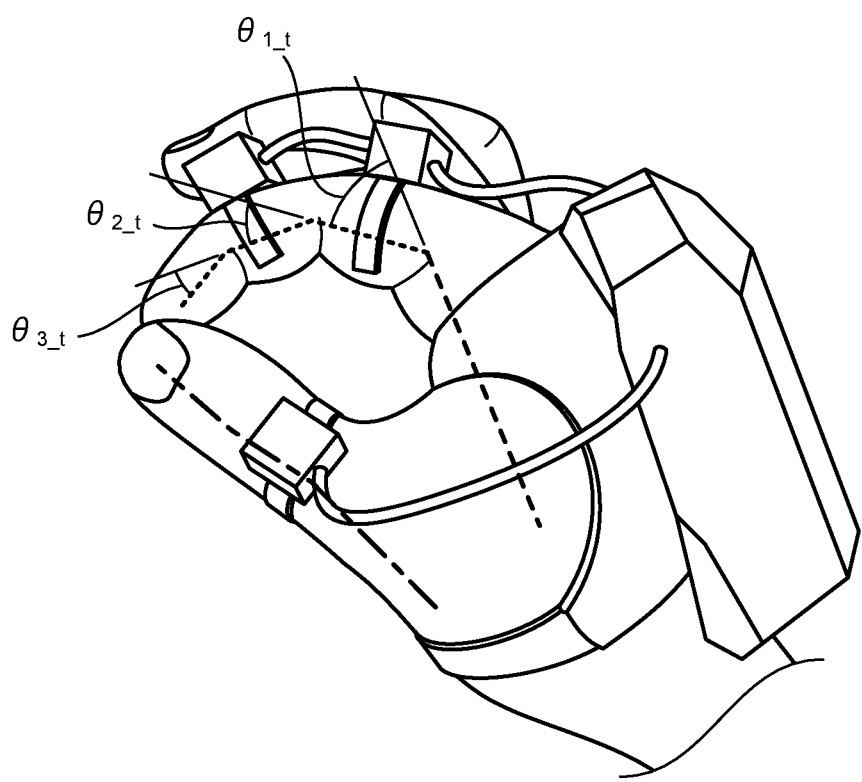
FIG. 5 is a view illustrating an example of a posture of a finger.

In addition, the controller 1 also performs "finger posture detection" of detecting a posture of a finger. FIG. 5 is a view illustrating an example of the posture of the finger. Postures of the thumb and the index finger are illustrated as an example of the postures of the fingers in FIG. 5. As illustrated in FIG. 5, the postures of the fingers are expressed by an angle of each joint of the fingers. For example, the posture of the index finger is expressed by an angle $\theta_{1\_f}$ at which a third joint is bent, an angle $\theta_{2\_f}$ at which a second joint is bent, and an angle $\theta_{3\_f}$ at which a first joint is bent. Note that the third joint is also referred to as a metacarpophalangeal joint (MP) joint, the second joint is also referred to as a proximal interphalangeal joint (PIJ) joint, and the first joint is also referred to as a distal interphalangeal joint (DIJ) joint.

2-1. Sensors Used for Fingertip Contact Detection

For the "fingertip contact detection", methods such as "electrostatic touch detection" of detecting fingertip contact from a change in electrostatic capacitance and "acceleration waveform detection" of detecting fingertip contact from a waveform of an acceleration sensor are applied as described in Background.

In the controller 1 according to the embodiment of the present disclosure, an example in which two methods that are the "electrostatic touch detection" and the "acceleration waveform detection" are used in combination will be described. For example, for the "electrostatic touch detection", a GND-side electrode 35A provided on the thumb part 30A and a potential detection-side electrode 35B provided on the index finger part 30B are used. For example, a conductive gasket is arranged on a surface of the central elastic member 33 included in the C-shaped locking member which surface is in contact with an upper surface portion of a proximal phalanx or a middle phalanx of a finger, whereby the electrode 35A and the electrode 35B are electrically connected to each other when the thumb and the index finger are in contact with each other. In addition, an acceleration sensor of an inertial measurement unit (IMU) mounted on the index finger part 30B is used for the "acceleration waveform detection".

2-2. Sensors used for finger posture detection

For the "finger posture detection", an IMU mounted on the controller main body 10, an IMU 37A mounted on the thumb part 30A, an IMU 37B mounted on the index finger part 30B, and an IMU 37C mounted on the index finger part 30C are used. Hereinafter, the IMU 37A, the IMU 37B, and the IMU 37C may be referred to as "IMUs 37" in a case where individual identification thereof is not necessary.

3. One aspect of a problem

As described in Background, since both of the "electrostatic touch detection" and the "acceleration waveform detection" have advantages and disadvantages, there is one aspect that it is difficult to robustly detect the fingertip contact.

For example, in the "acceleration waveform detection", it is difficult to robustly detect the timing at which the fingertips are separated from each other although the timing at which the fingertips come into contact with each other can be robustly detected. This is because a change in acceleration is small at the timing at which the fingertips are separated from each other and it is difficult to detect the timing at which the fingertips come into contact with each other although a change in acceleration is large at the timing at which the fingertips come into contact with each other and it is easy to detect the timing at which the fingertips come into contact with each other.

In addition, there is a slight change in electrostatic capacitance although the "electrostatic touch detection" is to detect the fingertip contact from the change in the electrostatic capacitance. Thus, since it is difficult to discriminate between a change in a value due to disturbance such as a deviation of a mounting position of the controller 1 or gripping of an object and a change in the value due to the contact between the fingertips, it is difficult to detect the timing at which the fingertips come into contact with each other.

4. One Aspect of an Approach to Problem Solving

Thus, in the controller 1 according to the embodiment of the present disclosure, the "acceleration waveform detection" is executed until the timing at which the fingertips come into contact with each other is detected, and the "electrostatic touch detection" is executed until the timing at which the fingertips are separated from each other is detected.

In such a manner, the "acceleration waveform detection" is executed until the timing at which the fingertips come into contact with each other is detected. Thus, a decrease in detection accuracy due to an influence of the disturbance such as the deviation of the mounting position of the controller 1 and the gripping of the object can be prevented, whereby the disadvantage of the "acceleration waveform detection" can be compensated by the advantage of the "electrostatic touch detection".

Furthermore, the "electrostatic touch detection" is executed until the timing at which the fingertips are separated from each other is detected. Thus, the detection omission of the timing at which the fingertips are separated from each other, which omission is due to smallness of the change in the acceleration, can be prevented from being generated, whereby the disadvantage of the "electrostatic touch detection" can be compensated by the advantage of the "acceleration waveform detection".

Thus, the controller 1 according to the embodiment of the present disclosure can make it possible to realize robust detection of the fingertip contact.

5. Functional Configuration of a Controller Main Body 10

Figure 6:
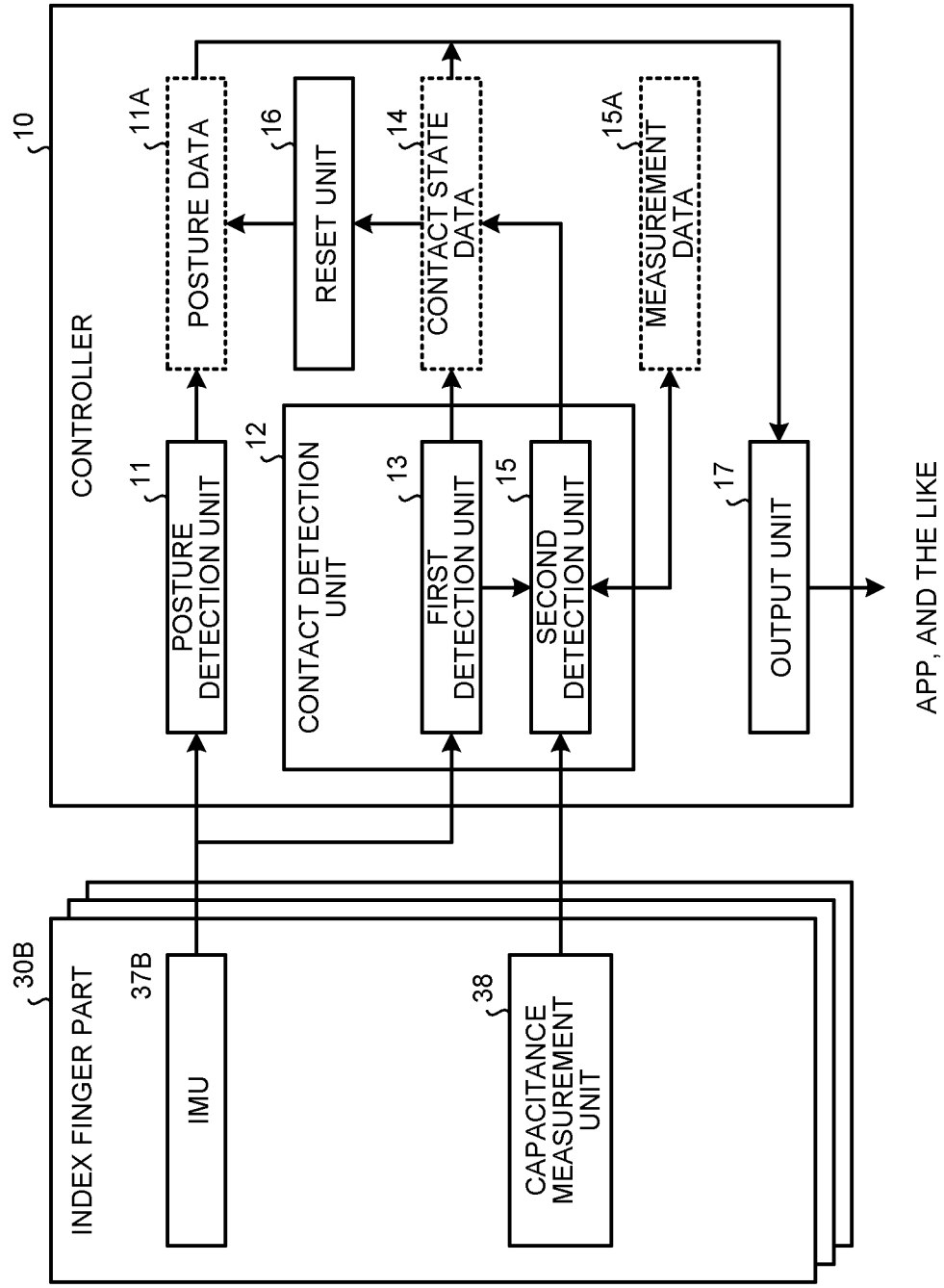
FIG. 6 is a block diagram illustrating an example of a functional configuration of a controller book according to the one embodiment.

FIG. 6 is a block diagram illustrating an example of the functional configuration of the controller main body 10 according to the one embodiment. In FIG. 6, among devices included in the controller 1, a part of functions included in the controller main body 10 and the finger parts 30 is schematically illustrated as solid-line blocks, and a part of information exchanged between functional units included in the controller main body 10 is schematically illustrated as broken-line blocks. Note that although a block of a function included in the index finger part 30B among the finger parts 30 is illustrated as a representative in FIG. 6, the other finger parts 30 are common except for a point that a electrostatic capacitance measurement unit 38 does not need to be included.

As illustrated in FIG. 6, the controller main body 10 includes a posture detection unit 11, an operation control unit 12, a reset unit 16, and an output unit 17.

The functional units such as the posture detection unit 11, the operation control unit 12, the reset unit 16, and the output unit 17 illustrated in FIG. 6 can be virtually realized by a hardware processor such as a central processing unit (CPU) or a micro processing unit (MPU). For example, the processor reads a program such as a detection program that realizes functions of the fingertip contact detection, the finger posture detection, and the like in addition to an operating system (OS) from a storage device (not illustrated) such as a read only memory (ROM). Then, the processor executes the detection program and expands processes corresponding to the functional units on a memory such as a random access memory (RAM). As a result, the functional units are virtually realized as the processes. Here, although the CPU and the MPU have been exemplified as the examples of the processor, the functional units may be realized by an arbitrary processor regardless of a general-purpose type or a specialized type. In addition, the above-described functional units may be realized by hard-wired logic such as an application specific integrated circuit (ASIC) or a field programmable gate array (FPGA).

Posture data 11A including angles $\theta_1$ to $\theta_3$ of respective joints of a finger, contact state data 14 corresponding to a status of either the ON state or the OFF state of the fingertip contact, and measurement data 15A are exemplified as data to be referred to or registered by the functional units. These various kinds of data are not necessarily stored in a main storage device such as the RAM, and a part or all of the data may be stored in a storage.

<5-1. Posture Detection Unit>

The posture detection unit 11 is a processing unit that detects a posture of a finger.

As the one embodiment, the posture detection unit 11 acquires IMU data from the IMUs 37 respectively mounted on the finger parts 30. Here, each of the IMUs 37 is a so-called inertial measurement device, and is a unit on which a gyroscope sensor, an acceleration sensor, and the like are mounted. For example, the IMU data transmitted from the IMUs 37 may include angular velocity in three axis and acceleration in three axes. As described above, every time the latest IMU data is acquired, the posture detection unit 11 updates the angle $\theta_1$ of the third joint, the angle $\theta_2$ of the second joint, and the angle $\theta_3$ of the first joint of the finger on the basis of the angular velocity and the acceleration included in the latest IMU data. Note that although an example in which the IMUs 37 include the gyroscope sensor and the acceleration sensor has been described herein, this is not a limitation and a geomagnetic sensor may be included.

For example, in a case of updating the posture of the index finger, the posture detection unit 11 calculates the angle $\theta_{1\_t}$ of the third joint by integrating angular velocity acquired from the IMU 37C to the angle $\theta_{1\_t-1}$ of the third joint which angle is included in the posture data 11A. At this time, the posture detection unit 11 can also correct gyro drift of the angle $\theta_{1\_t}$ of the third joint on the basis of an angle calculation value of the acceleration sensor which value is calculated on the basis of the integrated value of the acceleration which integrated value is acquired by integration of the acceleration acquired from the IMU 37C. Furthermore, the posture detection unit 11 updates the angle $\theta_2$ of the second joint on the basis of angular velocity and acceleration acquired from the IMU 37B, similarly to the update of the angle $\theta_1$ of the third joint. In a case of updating the angle $\theta_1$ of the third joint and the angle $\theta_2$ of the second joint of the finger, it is possible to set a limit to a range of an angle movable from the angle $\theta_{1\_t-1}$ of the third joint or an angle $\theta_{2\_t-1}$ of the second joint of previous time, or to set a movable range of extension and bending as a constraint condition.

Furthermore, the posture detection unit 11 can calculate the angle $\theta_3$ of the first joint on the basis of the angle $\theta_2$ of the second joint of the finger. For example, the posture detection unit 11 can calculate an estimation value of the angle $\theta_3$ of the first joint by multiplying the angle $\theta_2$ of the second joint of the finger by a coefficient that is set on the basis of interlocking of the angle $\theta_1$ of the third joint and the angle $\theta_2$ of the second joint of the finger with the angle $\theta_3$ of the first joint of the finger, and that is 0.7, for example. Note that although an example of updating the posture of the index finger has been described herein, it goes without saying that the posture of the thumb can be updated in a similar manner.

<5-2. Operation Control Unit>

The operation control unit 12 is a processing unit that adaptively switches and operates the "acceleration waveform detection" and the "electrostatic touch detection". For example, the operation control unit 12 executes the "acceleration waveform detection" until the timing at which the fingertips come into contact with each other is detected, and executes the "electrostatic touch detection" until the timing at which the fingertips are separated from each other is detected.

<5-2-1. First Detection Unit>

The first detection unit 13 is a processing unit that executes the "acceleration waveform detection".

As the one embodiment, the first detection unit 13 operates until the contact state data 14 transitions to the ON state after transitioning to the OFF state of the fingertip contact. For example, the first detection unit 13 can use, for the "acceleration waveform detection", a waveform measured by the acceleration sensor of the IMU 37B mounted on the index finger part 30B. Here, for the "acceleration waveform detection", a model that receives waveforms of the acceleration in the three axes as inputs, and outputs a label of a class of either the ON state or the OFF state of the contact state can be used. Learning algorithms such as deep learning, logistic analysis, a random forest, a support vector machine, and a decision tree can be applied to learning of such a model. For example, every time the latest acceleration is acquired, the first detection unit 13 inputs, to the model, a waveform of the acceleration acquired by going back for a predetermined period in the past from the time when the latest acceleration is acquired. As a result, a label, that is, the ON state or the OFF state of the contact state can be acquired as a detection result from the model. Then, in a case where the label of the ON state of the contact state is output from the model, the first detection unit 13 updates the contact state data 14 from the OFF state of the fingertip contact to the ON state.

<5-2-2. Second Detection Unit>

The second detection unit 15 is a processing unit that performs the "electrostatic touch detection".

As the one embodiment, the second detection unit 15 operates until the contact state data 14 transitions to the OFF state after transitioning to the ON state of the fingertip contact. For example, a frequency spectrum of a voltage value measured with the electrode 35B by the electrostatic capacitance measurement unit 38 of the index finger part 30B can be used for the "electrostatic touch detection". For example, the electrostatic capacitance measurement unit 38 can be configured as a circuit that detects a change in electrostatic capacitance between the fingertips of the thumb and the index finger by a change in a voltage value at the time of multi-frequency driving. That is, the electrostatic capacitance measurement unit 38 sweeps a frequency for driving a detection circuit (not illustrated) in a predetermined range such as 100 kHz to 1200 kHz. As a result, a measured voltage value is acquired from the electrode 35B for each sweep frequency. The frequency spectrum of the voltage value acquired in such a manner may be hereinafter referred to as "measurement data".

Here, at the time point at which the contact state data 14 is updated from the OFF state of the fingertip contact to the ON state, that is, at the timing at which the fingertips come into contact with each other, the second detection unit 15 stores measurement data before and after the time point as the measurement data 15A. As a result, the measurement data before the thumb and the index finger come into contact with each other and the measurement data after the thumb and the index finger come into contact with each other are stored as the measurement data 15A. Hereinafter, the measurement data before the thumb and the index finger come into contact with each other may be referred to as "measurement data at the time of non-contact", and the measurement data after the thumb and the index finger come into contact with each other may be referred to as "measurement data at the time of contact". The measurement data 15A stored in such a manner is used to identify the transition of the fingertip contact from the ON state to the OFF state.

For example, every time the latest measurement data is acquired from the electrostatic capacitance measurement unit 38 after the contact state data 14 is updated from the OFF state of the fingertip contact to the ON state, the second detection unit 15 performs the following processing. That is, the second detection unit 15 calculates similarity between the latest measurement data acquired from the electrostatic capacitance measurement unit 38 and the two pieces of measurement data included in the measurement data 15A. As an example of such similarity, a correlation coefficient between the pieces of measurement data can be calculated.

Figure 7A:
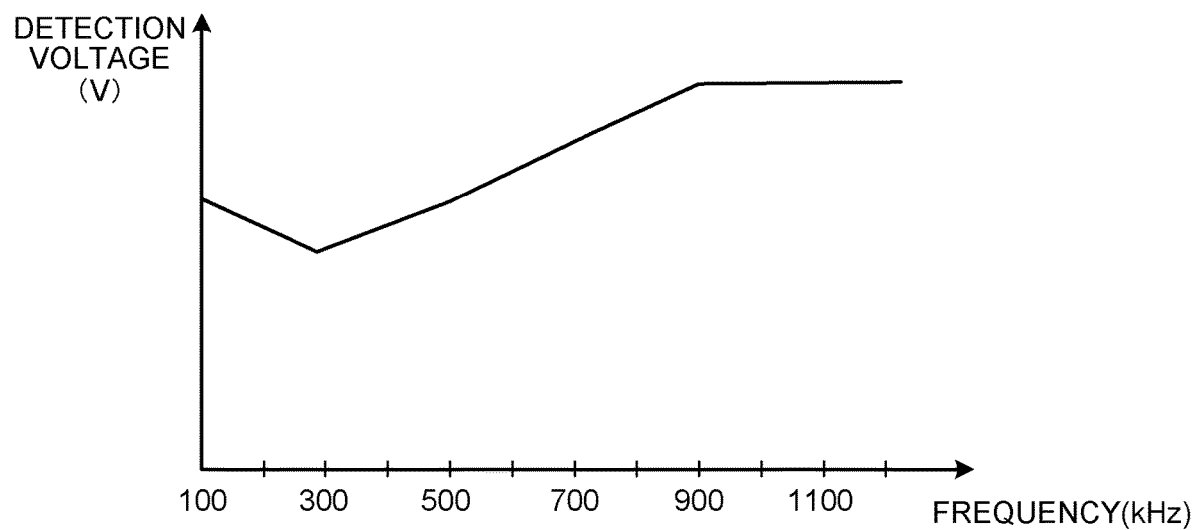
FIG. 7A is a graph illustrating an example of measurement data at the time of non-contact.
Figure 7B:
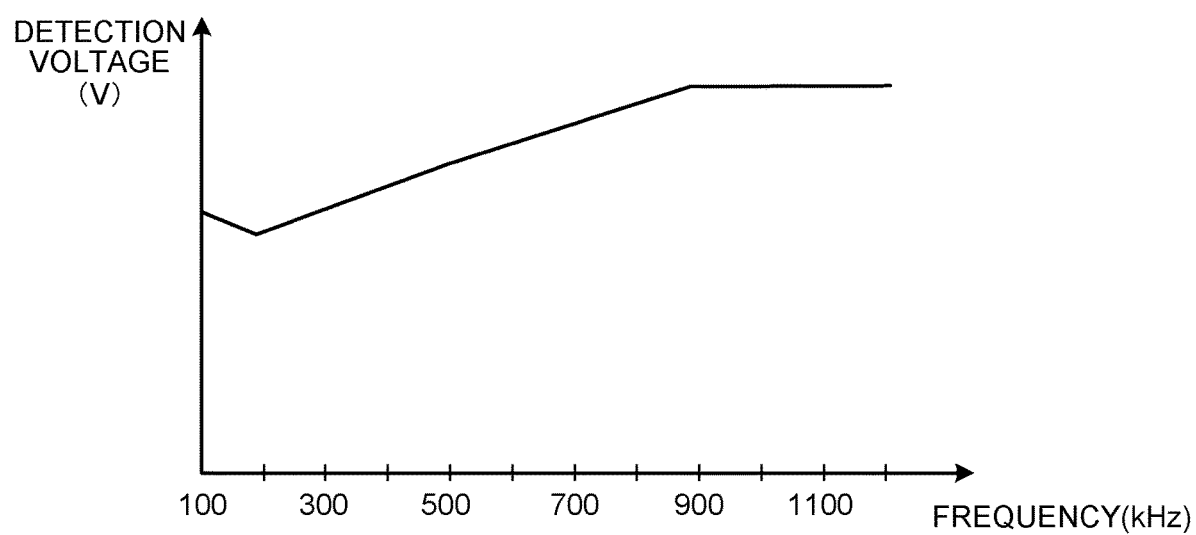
FIG. 7B is a graph illustrating an example of measurement data at the time of contact.

FIG. 7A is a graph illustrating an example of the measurement data at the time of non-contact. In addition, FIG. 7B is a graph illustrating an example of the measurement data at the time of contact. Vertical axes of the graphs illustrated in FIG. 7A and FIG. B indicate a voltage value, and horizontal axes thereof indicate a frequency (kHz). As illustrated in FIG. 7A and FIG. 7B, only a slight difference appears between the measurement data at the time of non-contact and the measurement data at the time of contact. For example, a point that a minimum value of the voltage value is observed around 200 kHz in the measurement data at the time of contact while a minimum value of the voltage value is observed around 300 kHz in the measurement data at the time of non-contact appears as a difference between the two. Along with this, a slight difference is also generated in a slope increasing from 300 kHz to 900 kHz.

Here, the second detection unit 15 determines whether the similarity between the latest measurement data and the measurement data at the time of non-contact is higher than the similarity between the latest measurement data and the measurement data at the time of contact. That is, the second detection unit 15 determines whether the latest measurement data is similar to either the measurement data at the time of non-contact illustrated in FIG. 7A or the measurement data at the time of contact illustrated in FIG. 7B. At this time, in a case where the latest measurement data is similar to the measurement data at the time of non-contact illustrated in FIG. 7A, it is possible to identify that the thumb and the index finger are separated. In this case, the second detection unit 15 updates the contact state data 14 from the ON state of the fingertip contact to the OFF state. On the other hand, in a case where the latest measurement data is similar to the measurement data at the time of contact illustrated in FIG. 7B, it is possible to identify that the thumb and the index finger are not separated. In this case, the second detection unit 15 keeps monitoring the latest measurement data acquired from the electrostatic capacitance measurement unit 38.

Note that although an example of using both the measurement data at the time of contact and the measurement data at the time of non-contact for the fingertip contact detection has been described herein, it is not necessary to use the both. For example, in a case where the similarity between the latest measurement data and the measurement data at the time of non-contact is equal to or higher than a predetermined threshold, it can be identified that the thumb and the index finger are separated. In addition, in a case where the similarity between the latest measurement data and the measurement data at the time of contact is lower than the predetermined threshold, it can be identified that the thumb and the index finger are separated.

Also, although an example in which the electrode 35A of the thumb part 30A is the GND electrode and the electrode 35B of the index finger part 30B is the detection electrode has been described herein, this is not a limitation. For example, the electrode 35A of the thumb part 30A can be used as a detection electrode, and the electrode 35B of the index finger part 30B can be used as a GND electrode. Furthermore, although an example of providing the electrodes on the thumb part 30A and the index finger part 30B has been described, an electrode may be provided on the controller main body 10. In this case, the electrode provided on the controller main body 10 may be a GND electrode or a detection electrode.

<5-3. Reset Unit>

The reset unit 16 is a processing unit that resets the posture data 11A.

The following two pieces of knowledge are motivation for the reset. First, there is knowledge that an accumulated error due to a gyroscope is likely to be generated in a change in a Yaw direction with respect to a ground in the posture detection on the index finger by the IMU since an acceleration sensor value does not change. Furthermore, as second one, there is knowledge that a finger posture of when the fingertip contact is made is substantially unchanged. On the basis of these pieces of knowledge, the posture of the index finger at the time of the fingertip contact, such as the angles of the third joint to the first joint of the index finger illustrated in FIG. 5 are stored for resetting before the accumulated error due to the gyroscope increases, for example, until an integrated value of the angular velocity in the Yaw direction reaches a predetermined value.

Then, every time the contact state data 14 is updated from the OFF state of the fingertip contact to the ON state, the reset unit 16 resets the angles of the third joint to the first joint of the index finger, which angles are included in the posture data 11A, to the angles of the third joint to the first joint of the index finger which angles are stored for the resetting.

FIG. 8 is a view illustrating an example of a method of resetting a posture of a finger. For example, in a case where an angular difference between a plane including the thumb and the index finger and a horizontal plane (XY plane) is within a predetermined range, the accumulated error due to the gyroscope is likely to increase. In this case, as illustrated in FIG. 8, an error between the angles of the third joint to the first joint of the index finger which angles are detected by the "finger posture detection" and actual angles of the third joint to the first joint of the index finger increases. Even when the accumulated error of the gyroscope is generated in such a manner, reset to the angles $\theta_{1\_t}$ to $\theta_{3\_t}$ of the third joint to the first joint of the index finger which angles are stored for the resetting is performed in a stage in which the transition of the fingertip contact from the OFF state to the ON state is detected by the "fingertip contact detection". As a result, the accumulated error of the gyroscope can be reduced.

Although a point that the fingertip contact transitions from the OFF state to the ON state has been exemplified herein as an example of a reset condition, a condition may be further added. For example, in a situation in which the plane including the thumb and the index finger is not close to the horizontal plane, the accumulated error due to the gyroscope hardly increases. Thus, a state in which the angular difference between the plane including the thumb and the index finger and the horizontal plane is within the predetermined range such as ±45 degrees continuing for a predetermined period such as 30 seconds or longer can be further added to the reset condition.

<5-4. Output Unit>

The output unit 17 is a processing unit that outputs the posture data 11A and the contact state data 14 to a predetermined output destination. Examples of the output destination include an application program and the like that controls AR content, VR content, and the like. Such an output destination is not limited to the inside of the controller main body 10, and examples thereof include external devices such as AR glasses/goggles, VR glasses/goggles, a smartphone, a tablet terminal, a wearable terminal, a personal computer, and various server devices.

<<6. Processing Procedure of the Controller 1>>

Figure 9:
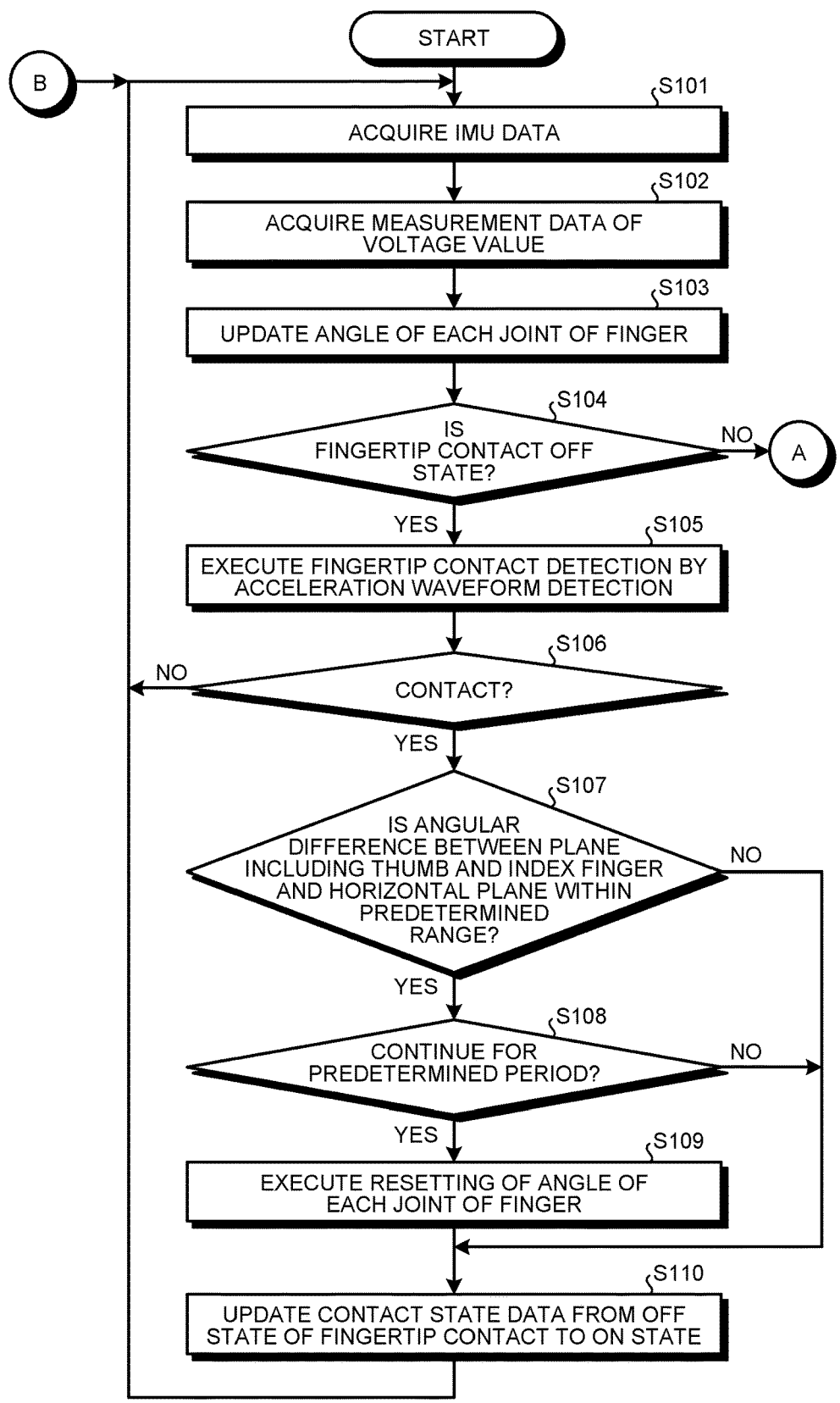
FIG. 9 is a flowchart (1) illustrating a processing procedure of a controller 1 according to the one embodiment.
Figure 10:
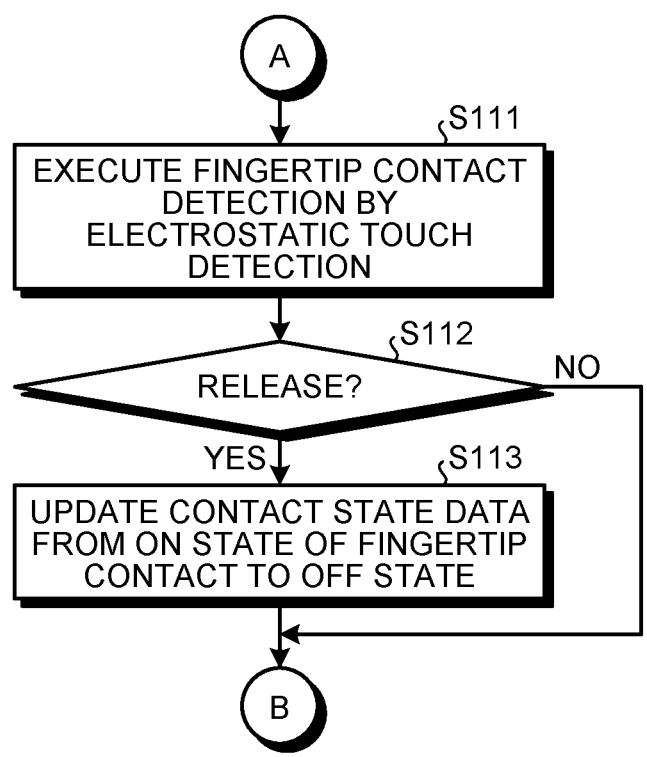
FIG. 10 is a flowchart (2) illustrating the processing procedure of the controller 1 according to the one embodiment.

FIG. 9 and FIG. 10 are flowcharts illustrating the processing procedure of the controller 1 according to the one embodiment. The processing illustrated in FIG. 9 and FIG. 10 is merely an example and is repeatedly performed in a case where the power of the controller main body 10 is in an ON state.

As illustrated in FIG. 9, IMU data is acquired from the IMU 37 mounted on each of the finger parts 30, and a frequency spectrum of a voltage value is acquired as measurement data from the electrostatic capacitance measurement unit 38 of the index finger part 30B (Step S101 and Step S102).

Then, the posture detection unit 11 updates the angle $\theta_1$ of the third joint, the angle $\theta_2$ of the second joint, and the angle $\theta_3$ of the first joint of the finger on the basis of angular velocity and acceleration included in the latest IMU data acquired in Step S101 (Step S103).

At this time, in a case where the contact state data 14 is set to the OFF state of the fingertip contact (Step S104 Yes), the first detection unit 13 executes the "acceleration waveform detection" (Step S105). For example, the first detection unit 13 can acquire a label output from the model, that is, the ON state or the OFF state of the contact state as a detection result by inputting, to the model, a waveform of acceleration acquired by going back for a predetermined period in the past from the time when the latest acceleration is acquired.

Then, in a case where the label of the ON state of the contact state is output from the model (Step S106 Yes), the reset unit 16 determines whether the state in which the angular difference between the plane including the thumb and the index finger and the horizontal plane is within the predetermined range such as ±45 degrees continues for predetermined time such as 30 seconds or longer (Step S107 and Step S108).

Here, in a case where the state in which the angular difference is within the predetermined range continues for the predetermined period or longer (Step S107 Yes and Step S108 Yes), the angles of the third joint to the first joint of the index finger, which angles are included in the posture data 11A, are reset to the angles of the third joint to the first joint of the index finger which angles are stored for the resetting (Step S109). Then, the first detection unit 13 updates the contact state data 14 from the OFF state of the fingertip contact to the ON state (Step S110), and transitions to the processing of Step S101 described above.

On the other hand, in a case where the angular difference is not within the predetermined range or the state in which the angular difference is within the predetermined range does not continue for the predetermined period or longer (Step S107 No or Step S108 No), the processing of Step S109 described above is skipped. Then, the first detection unit 13 updates the contact state data 14 from the OFF state of the fingertip contact to the ON state (Step S110), and transitions to the processing of Step S101 described above.

Note that although not illustrated in FIG. 9, when the contact state data 14 is updated from the OFF state of the fingertip contact to the ON state (at the time of execution of Step S110), the measurement data at the time of non-contact and the measurement data at the time of contact are stored as the measurement data 15A.

In addition, in a case where the contact state data 14 is set to the ON state of the fingertip contact (Step S104 No), the second detection unit 15 executes the "electrostatic touch detection", as illustrated in FIG. 10 (Step S111). For example, the second detection unit 15 determines whether the similarity between the latest measurement data and the measurement data at the time of non-contact is higher than the similarity between the latest measurement data and the measurement data at the time of contact.

At this time, in a case where the latest measurement data is similar to the measurement data at the time of non-contact, it is possible to identify that the thumb and the index finger are separated. In this case, the second detection unit 15 updates the contact state data 14 from the ON state of the fingertip contact to the OFF state (Step S112), and transitions to the processing of Step S101 described above.

On the other hand, in a case where the latest measurement data is similar to the measurement data at the time of contact illustrated in FIG. 7B, it is possible to identify that the thumb and the index finger are not separated. In this case, the processing of Step S112 described above is skipped, and the processing transitions to the processing in Step S101.

<<7. One Aspect of an Effect>>

As described above, the controller 1 according to the embodiment of the present disclosure executes the "acceleration waveform detection" until the timing at which the fingertips come into contact with each other is detected, and executes the "electrostatic touch detection" until the timing at which the fingertips are separated from each other is detected.

In such a manner, the "acceleration waveform detection" is executed until the timing at which the fingertips come into contact with each other is detected. Thus, a decrease in detection accuracy due to an influence of the disturbance such as the deviation of the mounting position of the controller 1 and the gripping of the object can be prevented, whereby the disadvantage of the "acceleration waveform detection" can be compensated by the advantage of the "electrostatic touch detection".

Furthermore, the "electrostatic touch detection" is executed until the timing at which the fingertips are separated from each other is detected. Thus, the detection omission of the timing at which the fingertips are separated from each other, which omission is due to smallness of the change in the acceleration, can be prevented from being generated, whereby the disadvantage of the "electrostatic touch detection" can be compensated by the advantage of the "acceleration waveform detection".

Thus, the controller 1 according to the embodiment of the present disclosure can realize robust detection of the fingertip contact.

<<8. Application Example>>

For example, a detection result of a posture of a finger can be utilized for the "fingertip contact detection". Even when it is determined that there is fingertip contact as the detection result of the "fingertip contact detection", the thumb and the index finger are not necessarily in contact with each other in some cases.

Figure 11:
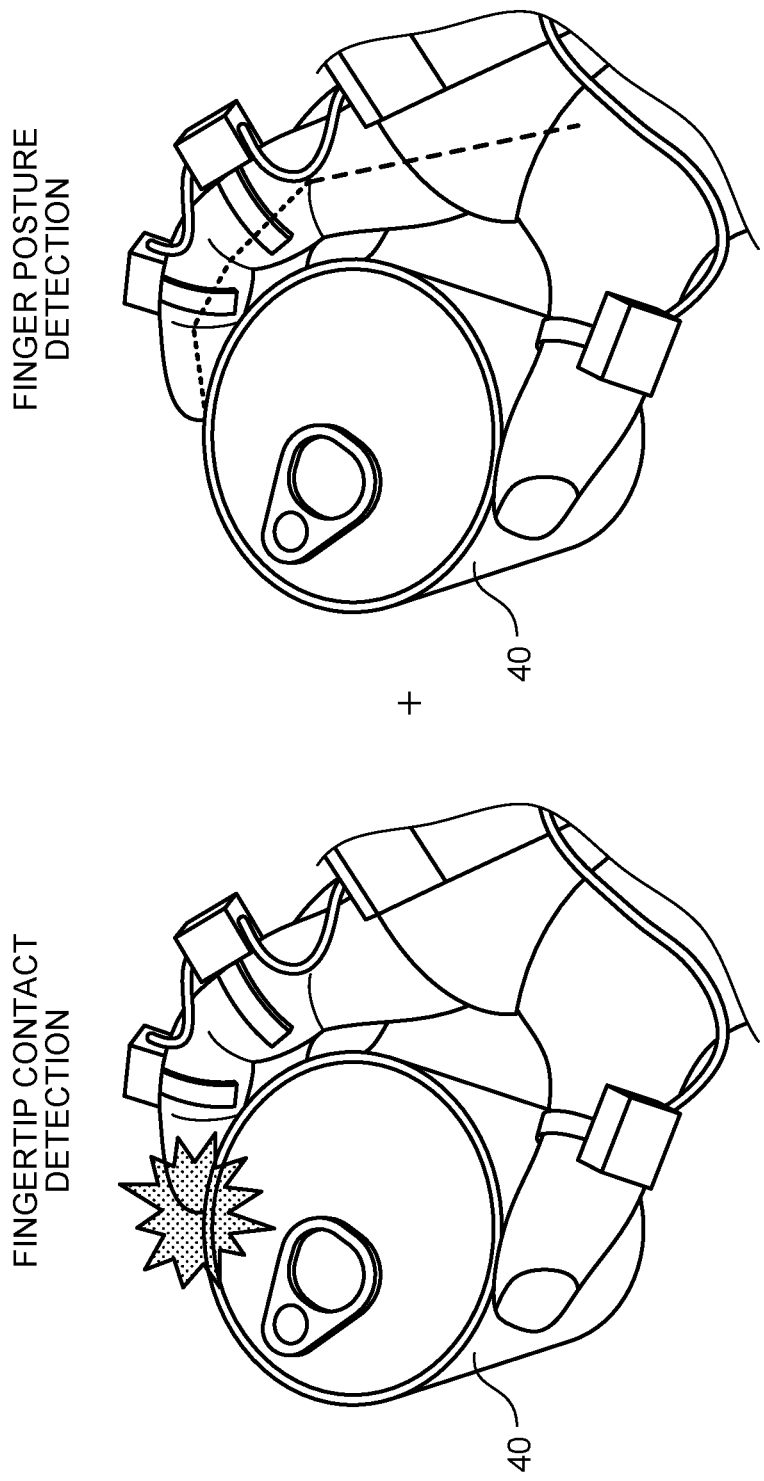
FIG. 11 is a view illustrating an application example of a detection result of the posture of the finger to fingertip contact detection.

FIG. 11 is a view illustrating an application example of the detection result of the posture of the finger to the fingertip contact detection. For example, as illustrated in FIG. 11, in a case where a conductor 40 is gripped by the thumb and the index finger, for example, in a case where the thumb and the index finger are electrically connected via the conductor 40, there is a case where it is determined that there is the fingertip contact as the detection result of the "fingertip contact detection". As described above, with the "fingertip contact detection" alone, even in a case where erroneous detection is generated, the generation of the erroneous detection can be prevented by control on validation or invalidation of the detection result of the "fingertip contact detection" on the basis of the detection result of the posture of the finger, as illustrated in FIG. 11.

For example, in a case where the angle of each joint of the finger which angle is acquired by the "finger posture detection" is not within a predetermined range from the posture of the index finger at the time of the fingertip contact which posture is stored in the memory and which is, for example, the angles of the third joint to the first joint of the index finger illustrated in FIG. 5, the second detection unit 15 invalidates a determination result indicating that there is the fingertip contact. In this case, it may be determined whether the angle is within the predetermined range from the angle at the time of the fingertip contact at every joint, or it may be determined whether the angle is within the predetermined range from the angle at the time of the fingertip contact only at a part of the joints. In addition, the second detection unit 15 may refer to a skeleton of the thumb, which skeleton is generated from the posture of the thumb, and a skeleton of the index finger which skeleton is generated from the posture of the index finger, and control the validation or invalidation of the determination result indicating that there is the fingertip contact depending on whether a distance between a far end of the skeleton of the thumb and a far end of the skeleton of the index finger is within a predetermined threshold. For example, the second detection unit 15 can invalidate the determination result indicating that there is the fingertip contact in a case where the distance between the far end of the skeleton of the thumb and the far end of the skeleton of the index finger is not within the predetermined threshold while validating the determination result indicating that there is the fingertip contact in a case where the distance between the far end of the skeleton of the thumb and the far end of the skeleton of the index finger is within the predetermined threshold.

<<9. Modification Example>>

The functions of the fingertip contact detection, the finger posture detection, and the like are not necessarily implemented as the controller device. For example, the processing illustrated in FIG. 9 and FIG. 10 may be executed by a general information processing device such as a smartphone, a tablet terminal, a wearable terminal, a personal computer, or a server device in addition to the AR glasses/goggles, the VR glasses/goggles, or the like connected to the controller 1 according to the embodiment of the present disclosure via the input/output interface, the communication interface, or the network.

Also, among the pieces of processing described in the above embodiment, all or a part of the processing described to be automatically performed can be manually performed, or all or a part of the processing described to be manually performed can be automatically performed by a known method. In addition, the processing procedures, specific names, and information including various kinds of data or parameters illustrated in the above document or in the drawings can be arbitrarily changed unless otherwise specified. For example, various kinds of information illustrated in each drawing are not limited to the illustrated information.

Also, each component of each of the illustrated devices is a functional concept, and does not need to be physically configured in the illustrated manner. That is, a specific form of distribution/integration of each device is not limited to what is illustrated in the drawings, and a whole or part thereof can be functionally or physically distributed/integrated in an arbitrary unit according to various loads and usage conditions.

Also, an effect in each of the embodiments described in the present description is merely an example and is not a limitation, and there may be a different effect.

<<10. Hardware Configuration>>

Figure 12:
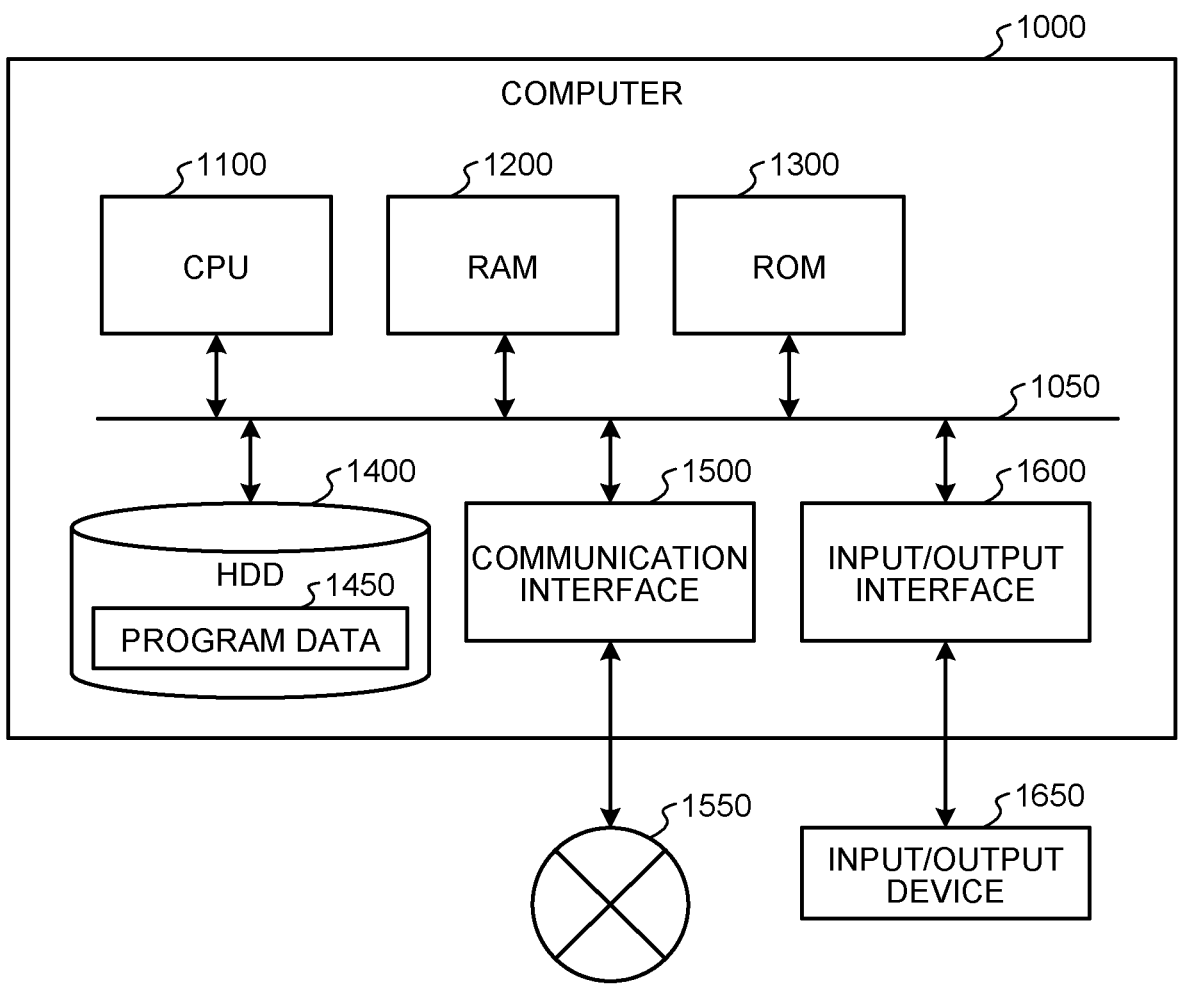
FIG. 12 is a hardware configuration diagram illustrating an example of a computer that realizes functions of an information processing device.

The information processing device according to each of the above embodiments is realized by, for example, a computer 1000 having a configuration in a manner illustrated in FIG. 12. In the following, the information processing device according to the embodiment will be described as an example. FIG. 12 is a hardware configuration diagram illustrating an example of the computer 1000 that realizes functions of the information processing device. The computer 1000 includes a CPU 1100, a RAM 1200, a read only memory (ROM) 1300, a hard disk drive (HDD) 1400, a communication interface 1500, and an input/output interface 1600. Each unit of the computer 1000 is connected by a bus 1050.

The CPU 1100 operates on the basis of programs stored in the ROM 1300 or the HDD 1400, and controls each unit. For example, the CPU 1100 expands the programs, which are stored in the ROM 1300 or the HDD 1400, in the RAM 1200 and executes processing corresponding to the various programs.

The ROM 1300 stores a boot program such as a basic input output system (BIOS) executed by the CPU 1100 during activation of the computer 1000, a program that depends on hardware of the computer 1000, and the like.

The HDD 1400 is a computer-readable recording medium that non-temporarily records a program executed by the CPU 1100, data used by the program, and the like. Specifically, the HDD 1400 is a recording medium that records the information processing program according to the present disclosure which program is an example of program data 1450.

The communication interface 1500 is an interface with which the computer 1000 is connected to an external network 1550 (such as the Internet). For example, the CPU 1100 receives data from another equipment or transmits data generated by the CPU 1100 to another equipment via the communication interface 1500.

The input/output interface 1600 is an interface to connect an input/output device 1650 and the computer 1000. For example, the CPU 1100 receives data from an input device such as a keyboard or mouse via the input/output interface 1600. Also, the CPU 1100 transmits data to an output device such as a display, speaker, or printer via the input/output interface 1600. Also, the input/output interface 1600 may function as a medium interface that reads a program or the like recorded on a predetermined recording medium (medium). The medium is, for example, an optical recording medium such as a digital versatile disc (DVD) or phase change rewritable disk (PD), a magneto-optical recording medium such as a magneto-optical disk (MO), a tape medium, a magnetic recording medium, a semiconductor memory, or the like.

For example, in a case where the computer 1000 functions as the information processing device according to the embodiment, the CPU 1100 of the computer 1000 realizes each functional unit included in the controller main body 10 by executing the information processing program loaded on the RAM 1200. Also, the HDD 1400 stores the information processing program according to the present disclosure, and data in a content storage unit 121. Note that the CPU 1100 reads the program data 1450 from the HDD 1400 and performs execution thereof, but may acquire these programs from another device via the external network 1550 in another example.

Note that the present technology can also have the following configurations.

(1)

An information processing device comprising:
  a first detection unit that detects contact of fingertips on a basis of an output waveform of an acceleration sensor;
  a second detection unit that detects the contact of the fingertips on a basis of a change in electrostatic capacitance; and
  an operation control unit that causes the first detection unit to operate in a case of detecting timing at which the fingertips come into contact with each other, and causes the second detection unit to operate in a case of detecting timing at which the fingertips are separated from each other.

(2)

The information processing device according to claim (1), wherein
  the second detection unit detects timing at which a thumb and an index finger are separated by using measurement data acquired by sweeping of a frequency for measuring a potential between an electrode mounted on a side of the thumb and an electrode mounted on a side of the index finger within a predetermined range.

(3)

The information processing device according to claim (2), wherein
  the second detection unit detects the timing at which the thumb and the index finger are separated by using measurement data at a time of non-contact which data is measured before timing at which the thumb and the index finger come into contact with each other is detected and measurement data at a time of contact which data is measured after the timing at which the thumb and the index finger come into contact with each other is detected.

(4)
The information processing device according to claim (3), wherein
the second detection unit detects the timing at which the thumb and the index finger are separated according to whether similarity between latest measurement data and the measurement data at the time of non-contact is higher than similarity between the latest measurement data and the measurement data at the time of contact.

(5)
The information processing device according to claim (2), wherein
the second detection unit detects the timing at which the thumb and the index finger are separated by using measurement data at a time of non-contact which data is measured before timing at which the thumb and the index finger come into contact with each other is detected.

(6)
The information processing device according to claim (5), wherein
the second detection unit detects the timing at which the thumb and the index finger are separated according to whether similarity between latest measurement data and the measurement data at the time of non-contact is equal to or higher than a predetermined threshold.

(7)
The information processing device according to claim (2), wherein
the second detection unit detects the timing at which the thumb and the index finger are separated by using measurement data at a time of contact which data is measured after timing at which the thumb and the index finger come into contact with each other is detected.

(8)
The information processing device according to claim (7), wherein
the second detection unit detects the timing at which the thumb and the index finger are separated according to whether similarity between latest measurement data and the measurement data at the time of contact is lower than a predetermined threshold.

(9)
The information processing device according to any one of (1) to (8), further comprising:
a posture detection unit that detects a posture of a finger on a basis of data of a motion sensor; and
a reset unit that resets, in a case where the timing at which the fingertips come into contact with each other is detected by the first detection unit, the posture of the finger, which posture is detected by the posture detection unit, to a posture of the finger which posture is stored for resetting.

(10)
The information processing device according to claim (9), wherein
the reset unit executes the resetting in a case where an angular difference between a plane including a thumb and an index finger and a horizontal plane is within a predetermined range.

(11)
The information processing device according to claim (9), wherein
the reset unit executes the resetting in a case where a state in which an angular difference between a plane including a thumb and an index finger and a horizontal plane is within a predetermined range continues for a predetermined period or longer.

(12)
The information processing device according to any one of (9) to (11), wherein
the posture of the finger is an angle of each joint of the finger.

(13)
The information processing device according to any one of (9) to (12), wherein
the second detection unit detects the timing at which the fingertips are separated from each other on a basis of a detection result of the posture of the finger by the posture detection unit.

(14)
The information processing device according to claim (2), wherein
a locking member on which the electrode on the side of the thumb or the electrode on the side of the index finger is mounted is formed in a manner of being mountable from an upper portion of a proximal phalanx or a middle phalanx of a finger.

(15)
The information processing device according to claim (14), wherein
the locking member supports an upper surface portion and a side surface portion of the proximal phalanx or the middle phalanx of the finger at three points that are elastic members respectively formed at both end portions of a C shape and an elastic member in which the electrode on the side of the thumb or the electrode on the side of the index finger is formed at a central portion of the C shape.

(16)
An information processing method comprising: executing, by a computer, processing of
causing a first detection unit that detects contact of fingertips on a basis of an output waveform of an acceleration sensor to operate in a case of detecting timing at which the fingertips come into contact with each other, and causing a second detection unit that detects the contact of the fingertips on a basis of a change in electrostatic capacitance to operate in a case of detecting timing at which the fingertips are separated from each other.

(17)
An information processing program causing a computer to execute processing of
causing a first detection unit that detects contact of fingertips on a basis of an output waveform of an acceleration sensor to operate in a case of detecting timing at which the fingertips come into contact with each other, and causing a second detection unit that detects the contact of the fingertips on a basis of a change in electrostatic capacitance to operate in a case of detecting timing at which the fingertips are separated from each other.

REFERENCE SIGNS LIST

1 CONTROLLER
10 CONTROLLER MAIN BODY
11 POSTURE DETECTION UNIT
12 OPERATION CONTROL UNIT
13 FIRST DETECTION UNIT
15 SECOND DETECTION UNIT
16 RESET UNIT
17 OUTPUT UNIT
30A THUMB PART
30B, 30C INDEX FINGER PART

The invention claimed is:

1. An information processing device, comprising:
a first detection unit configured to detect a contact of fingertips based on an output waveform of an acceleration sensor;
a second detection unit configured to detect the contact of the fingertips based on a change in an electrostatic capacitance; and
an operation control unit configured to:
control the first detection unit to operate at a timing at which the fingertips come into contact with each other, and
control the second detection unit to operate at a timing at which the fingertips are separated from each other.

2. The information processing device according to claim 1, wherein
the second detection unit is further configured to detect a timing at which a thumb and an index finger are separated based on measurement data, and
the measurement data is acquired by sweeping of a frequency, to measure a potential between an electrode mounted on a side of the thumb and an electrode mounted on a side of the index finger, within a predetermined range.

3. The information processing device according to claim 2, wherein
the measurement data includes a first measurement data and a second measurement data, and
the second detection unit is further configured to detect the timing at which the thumb and the index finger are separated based on
the first measurement data which is measured before a timing at which the thumb comes into contact with the index finger is detected and
the second measurement data which is measured after the timing at which the thumb comes into contact with the index finger is detected.

4. The information processing device according to claim 3, wherein the second detection unit is further configured to detect the timing at which the thumb and the index finger are separated based on whether a similarity between latest measurement data and the first measurement data is higher than a similarity between the latest measurement data and the second measurement data.

5. The information processing device according to claim 2, wherein
the measurement data includes a first measurement data and a second measurement data, and
the second detection unit is further configured to detect the timing at which the thumb and the index finger are separated based on the first measurement data which is measured before a timing at which the thumb comes into contact with the index finger is detected.

6. The information processing device according to claim 5, wherein the second detection unit is further configured to detect the timing at which the thumb and the index finger are separated based on whether a similarity between latest measurement data and the first measurement data is equal to or higher than a specific threshold.

7. The information processing device according to claim 2, wherein
the measurement data includes a first measurement data and a second measurement data, and
the second detection unit is further configured to detect the timing at which the thumb and the index finger are separated based on the second measurement data which is measured after a timing at which the thumb comes into contact with the index finger is detected.

8. The information processing device according to claim 7, wherein the second detection unit is further configured to detect the timing at which the thumb and the index finger are separated based on whether a similarity between latest measurement data and the second measurement data is lower than a specific threshold.

9. The information processing device according to claim 2, wherein a locking member on which the electrode on the side of the thumb or the electrode on the side of the index finger is mounted is formed in a manner of being mountable from an upper portion of a proximal phalanx or a middle phalanx of a finger.

10. The information processing device according to claim 9, wherein
the locking member supports an upper surface portion and a side surface portion of the proximal phalanx or the middle phalanx of the finger at three points,
the three points are
elastic members respectively formed at both end portions of a C shape and
an elastic member in which the electrode on the side of the thumb or the electrode on the side of the index finger is formed at a central portion of the C shape.

11. The information processing device according to claim 1, further comprising:
a posture detection unit configured to detect a posture of a finger based on data of a motion sensor; and
a reset unit configured to reset, based on the detection of the timing at which the fingertips come into contact with each other, the detected posture of the finger to a posture of the finger which is stored for resetting.

12. The information processing device according to claim 11, wherein the reset unit is further configured to reset the detected posture based on an angular difference, between a plane including a thumb and an index finger and a horizontal plane, being within a specific range.

13. The information processing device according to claim 11, wherein the reset unit is further configured to reset the detected posture based on a state in which an angular difference, between a plane including a thumb and an index finger and a horizontal plane, being within a specific range continuously for one of a specific period or longer than the specific period.

14. The information processing device according to claim 11, wherein the posture of the finger is an angle of each joint of the finger.

15. The information processing device according to claim 11, wherein the second detection unit is further configured to detect the timing at which the fingertips are separated from each other based on a detection result of the detection of the posture of the finger by the posture detection unit.

16. An information processing method, comprising
controlling a first detection unit, that detects a contact of fingertips based on an output waveform of an acceleration sensor, to operate at a timing at which the fingertips come into contact with each other; and
controlling a second detection unit, that detects the contact of the fingertips based on a change in electrostatic capacitance, to operate at a timing at which the fingertips are separated from each other.

17. A non-transitory computer-readable medium having stored thereon, computer-executable instructions which, when executed by a computer, cause the computer to execute operations, the operations comprising:
  controlling first detection unit, that a detects contact of fingertips based on an output waveform of an acceleration sensor, to operate at a timing at which the fingertips come into contact with each other; and
  controlling a second detection unit, that detects the contact of the fingertips based on a change in electrostatic capacitance, to operate at a timing at which the fingertips are separated from each other.

18. An information processing device, comprising:
  a first detection unit configured to detect a contact between a thumb and an index finger based on an output waveform of an acceleration sensor;
  a second detection unit configured to:
    detect the contact between the thumb and the index finger based on a change in an electrostatic capacitance;
    detect a timing at which the thumb and the index finger are separated based on measurement data, wherein the measurement data is acquired by sweeping of a frequency, to measure a potential between an electrode mounted on a side of the thumb and an electrode mounted on a side of the index finger, within a predetermined range, and
    the measurement data includes a first measurement data and a second measurement data; and
    detect the timing at which the thumb and the index finger are separated based on
      the first measurement data which is measured before a timing at which the thumb comes into contact with the index finger is detected and
      the second measurement data which is measured after the timing at which the thumb comes into contact with the index finger is detected and
  an operation control unit configured to:
    control the first detection unit to operate at the timing of the contact between the thumb and the index finger, and
    control the second detection unit to operate at the timing at which the thumb and the index finger are separated.

* * * * *